United States Patent [19]

Galinat

[11] 4,051,629
[45] Oct. 4, 1977

[54] HYBRID SEED PRODUCTION
[75] Inventor: Walton C. Galinat, Waben, Mass.
[73] Assignee: Research Corporation, New York, N.Y.
[21] Appl. No.: 676,372
[22] Filed: Apr. 12, 1976
[51] Int. Cl.$^2$ ............................................... A01H 1/02
[52] U.S. Cl. .................................... 47/58; 47/DIG. 1
[58] Field of Search .............................. 47/58, DIG. 1
[56] References Cited
PUBLICATIONS Progress in Corn Production, 1950, ASTA, p. 14.
The Evolution of the American Maydeae, Rao et al., 1974, Journ. of Heredity, 65:335–340 (1974), copy in Natl. Agric. Library.
Report from Ne-66 Subcommittee on Evolution & Morphology, Nov. 19, 1974, Galinat, p. 2.
Letter from W.C. Galinat to U.S. Dept. of Commerce, Feb. 12, 1976, copy in Director's Files.

Primary Examiner—Robert E. Bagwill
Attorney, Agent, or Firm—Hume, Clement, Brinks, Willian & Olds, Ltd.

[57] ABSTRACT

The use of alien chromosomes from Tripsacum to mask the expression of undesirable recessive traits in the production of hybrid corn seed is disclosed. When an alien addition monosome is used as a parent in a hybrid cross, the low transmission rate of the alien chromosome results in the expression of desirable traits in the progeny which were masked with the undesirable traits.

13 Claims, No Drawings

HYBRID SEED PRODUCTION

BACKGROUND OF THE INVENTION

Various recessive mutants in corn, particularly those expressed in the endosperm (e.g., shrunken, brittle, opaque, waxy, etc.), which improve the quality of the corn in such respects as sweetness, flavor and nutritive value are often impractical for large scale commercial use. This is because they are associated with undesirable production traits such as low germination and disease susceptibility.

An example involves the use of the recessive combination sugary-shrunken 2 (su $sh_2$) which results in so-called "ultra-sweet" corn. Although the homozygous su $sh_2$ combination results in 100% extra sweet kernels, typically considered too sweet and lacking "corn" taste and texture, it has been suggested that a "bi-sweet" hybrid can be produced using that combination as one of the parents. As I pointed out in Maize Genetics Cooperation News Letter 49: 98–99 Apr. 15, 1975), the crossing of the double recessive su $sh_2$ with a normal sweet corn (su $Sh_2$) would result in seed which, when planted by the farmer, would produce a crop ear segregating for approximately 25% ultra-sweet kernels and 75% normal sweet kernels. Such a "bi-sweet" corn has high commercial potential, especially for canning.

The drawback to such a system is that the su $sh_2$ combination has an uneconomically low germination rate (in the neighborhood of 10%). Part of this problem may be overcome by using a normal sweet corn (having normal germination) as one of the parents (preferably the seed parent) in the final cross to produce the "bi-sweet" hybrid discussed above. However, the homozygous su $sh_2$ parent seed remains defective from a germination standpoint, requiring either costly nurturing or an uneconomical 10-fold increase in the amount of seed required to grow the requisite number of parent plants.

Accordingly, there exists a need to overcome the expression of undesirable production traits which are associated with desirable traits in corn.

SUMMARY OF THE INVENTION

Tripsacum, the second closest relative of corn, has a normal complement of 18 chromosomes, as opposed to 10 for corn. It has long been known that Tripsacum and corn could be experimentally hybridized, and there have been many studies involving the identification, transmission and behavior of Tripsacum chromosomes as alien chromosome additions to corn. The presence of an alien Tripsacum chromosome in corn can be identified by its ability to suppress a known corn recessive. Techniques for incorporating a single extra Tripsacum chromosome (alien addition monosome) or an extra pair (alien addition disome) into a selected corn background are described in Galinat, "Intergenomic Mapping of Maize, Teosinte and Tripsacum", *Evolution*, Vol 27, No. 4, pp. 644–655 (Jan. 31, 1974) and Rao & Galinat, "The Evolution of the American Maydeae," *The Journal of Heredity* 65:335 –340(1974).

It has been found that certain Tripsacum chromosomes carry dominant alleles for certain recessive corn genes. For example, as pointed out in *Evolution* reference at page 649, the seventh chromosome of Tripsacum (Tr7) carries the dominant starchy allele Su. I reported to the members of the Technical Committee and Industry Representatives in 1973 and 1974 (see "Report From Ne-66 Subcommittee on Evolution and Morphology" dated November 19, 1974) that:

As reported last year, we are incorporating an extra pair of Tripsacum chromosomes (Tr7) carrying the starchy (Su) allele into a double recessive, sugary shrunken background. This makes possible a practical su sh2 seed type from the production point of view because it has full transmission of the extra Su bearing Tripsacum chromosome pair when in the 20+2 condition. When these extra chromosomes are reduced to the 20+1 state in the crop, their transmission drops down to about 8 to 10 percent and thereby, largely uncovering the sugary shrunken condition and normal sugary condition. The percent starchy in the farmers crop can be reduced to less than 1% if a line cross or three-way cross is used. In this case the su-sh2 Tr7 (20+2) male is previously crossed to a pseudo starcy sh2 (20+2) stock which would place the extra Su bearing Tr7 chromosome in the 20+1 condition in all pollinator plants. The seed would carry about 8% Tr7 and the farmers crop 8% of 8% or 0.64% Tr7. This would give fewer starchy kernels than normally occurs from contamination by field corn.

The present invention contemplates a method wherein an alien Tripsacum chromosome having the ability to mask an undesirable recessive trait in corn is incorporated into the corn. The low transmission of the alien chromosome to the progeny results in unmasking the undesirable trait, which is beneficial if the undesirable trait is associated with a desirable one. Alternatively, if it is desired to continue the masking in later generations, the alien chromosome addition can be maintained by selecting endosperm which phenotypically reflect the presence of the chromosome. Thus, what has heretofore been merely the subject of scholarly interest can, through specific manipulation in accordance with the method of the present invention, be utilized to solve significant production problems in the commercial production of hybrid corn seed.

DETAILED DESCRIPTION

The method of the present invention will be described by reference to specific examples involving its utilization in the commercial production of hybrid sweet corn seed, particularly the so-called bi-sweet hybrid previously described. It should be understood, however, that the invention is in no way limited to the specific examples discussed herein. In particular, the invention is not limited to any specific Tripsacum chromosome, nor to any specific recessive mutant characters expressed in the endosperm or otherwise, not to sweet corn. Consistent with the existence, identification and isolation of appropriate Tripsacum chromosomes, it may be possible to employ the method of the present invention wherever it is important to mask the expression of a recessive gene system.

As an example of the use of the present invention, assume a producer of hybrid sweet corn seed wishes to produce seed which, when planted, will yield a bi-sweet crop ear segregating for 75% normal sweet corn kernels (su Sh2) and 25% ultra-sweet kernels (su sh2). To accomplish this he will cross a parent which is homozygous for the recessive combination sugary-shrunken 2 (su sh2) with a normal sweet corn (su sh2). Ordinarily, the production of commercial quantities of the homozygous parent is prohibitively expensive due to the near-lethal character of the recessive combination su sh2, which results in extremely poor germination (about 10%). Accordingly, in order to maintain and increase the homozygous inbred parent, the producer is forced either to nuture the stock, or to plant several times the amount of seed which would normally be required.

This problem may be overcome, however, through the use of the present invention. In accordance with the invention, the producer selects a corn which is homozygous for the recessive combination su sh2 and incorporates therein a single extra seventh chromosome of Tripsacum. The resultant alien addition monosome corn, which has the genotype su sh2: Tr7(1), possesses normal germination qualities due to the presence of the dominant starchy allele Su on Tr7. This dominant gene suppresses the sugary su recessive and thus makes the poor germination trait of the su sh2 combination.

When the alien addition monosome corn (su sh2: Tr7(1)) is crossed with normal sweet corn (su Sh2), the resultant progeny (su su sh2 Sh2) may be harvested as corn seed. It is of course preferable (but not required) to use the alien addition monosome inbred as the pollen parent in the cross. Due to the nature of Tripsacum chromosomes, only about 8% of the alien Tr7 is transmitted to the progeny (su su sh2 Sh2). In other words, only about 8% of the seed harvested by the producer will contain the extra Tr7 chromosome with its starchy Su allele. If all this seed is grown by the farmer, the 8% transmission rate will carry over to his harvested crop, resulting in less than 1% starchy kernels. Even this small amount of contamination can be eliminated, if desired, by the producer. Since the starchy endosperm (which reflects the presence of the Tr7 chromosome) is readily recognizable, the producer can eliminate it from the harvested corn seed.

The alien addition monosome (su sh2: Tr7(1)) can be maintained or increased by inbreeding. The progeny of the selfing will again experience a low transmission rate for the alien Tr7 chromosome; however, the selfed progeny can again be differentiated by phenotypically selecting the starchy fraction for further use.

To obtain sufficient quantities of the alien addition monosome (su su2: Tr7(1)), the producer may wish to start with an alien addition disome (su su2: Tr7(2)). The disomic version may be increased by line crossing with a nutured stock of the homozygous recessive inbred su sh2. It is of course desirable (but not required) to employ the nutured stock as the pollen parent in the line cross. The line cross results in divorcing the original extra pair of Tr7 chromosomes in the disomic version, thus achieving the desired monosomic version.

Thus, in accordance with the method of the present invention, the appropriate alien Tripsacum chromosome is utilized to mask an undesirable production trait (low germination) during the production stage for the benefit of the producer. Although this masking effect also temporarily suppresses a desirable endosperm trait (ultra-sweet), it is later uncovered for the benefit of the consumer due to the low rate of transmission of the alien chromosome when it is present as a single extra.

Another example involves the recessive combination su shl wx which exhibits both desirable and undesirable traits. It has been found that the fifth chromosome of Tripsacum carries not only the dominant Shl Wx alleles, but also the dominant allele C which controls aleurone color. Although an alien addition disomic corn involving Tr5 is largely male sterile, the monosomic version is fully fertile. Thus the monosomic inbred su shl wx c: Tr5(1), with the undesirable trait masked by Tr5, may be crossed with a standard sweet corn of genotype su Shl Wx c. The progeny of the cross is harvested as corn seed and the purple kernels (reflecting the transmission of Tr5 with its dominant C allele) are removed. Thus the desirable trait is completely unmasked and segregates on the crop ear in the expected ratio when the remaining (non-purple) seed is planted.

I claim:

1. A method for masking the expression of an undesirable recessive trait in the production of hybrid corn comprising the steps of:
   selecting a corn which is homozygous for said trait;
   incorporating into said corn a Tripsacum chromosome which has the dominant allele for said trait and which also has the capability of genetically interacting with said corn to produce, upon selfing, an endosperm phenotype sufficiently recognizable to determine whether said endosperm carries said chromosome; and
   selfing said corn to increase said endosperm carrying said chromosome.

2. A method for producing hybrid corn seed comprising the steps of:
   selecting a first corn having a homozygous recessive gene system which results in the expression of a desirable trait and an undesirable trait;
   incorporating into said first corn a Tripsacum chromosome having the capability of masking said undesirable trait;
   crossing said first corn as either parent with a second corn having a gene system capable of interacting with the gene system of said first corn to produce corn seed which does not carry said chromosome and which either has said desirable trait or will produce some offspring having said desirable trait; and
   harvesting said corn seed.

3. A method for producing hybrid corn seed comprising the steps of:
   selecting a first corn having a homozygous recessive gene system which results in the expression of a desirable trait and an undesirable trait;
   obtaining an alien addition monosomic version of said first corn containing a Tripsacum chromosome capable of inhibiting the expression of said undesirable trait;
   crossing said alien addition monosomic version as either parent with a second corn to produce corn seed at least a portion of which does not carry said chromosome and either has or will produce some offspring which have said desirable trait.

4. The method of claim 3 wherein said alien addition monosomic version is obtained by line crossing an alien addition disomic version of said corn having a pair of said Tripsacum chromosomes with said first corn as either parent.

5. The method of claim 3 including the further step of maintaining the alien addition monosomic version by selfing and selecting from the progeny for further use the endosperm which reflects transmission of said Tripsacum chromosome.

6. A method for producing hybrid sweet corn seed comprising the steps of:
   selecting a first corn which is homozygous for the recessive combination sugary-shrunken 2 (genotype su sh2);

incorporating into said corn the seventh chromosome of Tripsacum to obtain an alien addition monosome corn (genotype su sh2: Tr7(1));

crossing said alien addition monosome corn as either parent with a sweet corn (genotype su Sh2) to obtain hybrid sweet corn seed; and harvesting said seed.

7. The method of claim 6 including the further step of removing from the harvested seed that proportion of the endosperm which reflects transmission of the seventh chromosome of Tripsacum.

8. The method of claim 6 including the further step of maintaining the alien addition monosome corn by selfing and selecting from the progeny for further use the endosperm which reflects transmission of the seventh chromosome of Tripsacum.

9. The method of claim 6 wherein said alien addition monosome corn is obtained by line crossing an alien addition disome corn of genotype su sh2: Tr7(2) as either parent with said first corn (genotype su sh2).

10. The method of claim 9 wherein said alien addition disome corn is employed as the female parent in said line cross.

11. The method of claim 6 wherein said alien addition monosome corn is employed as the male parent in the cross with said sweet corn.

12. A method for producing hybrid sweet corn seed comprising the steps of:

selecting a first corn which is homozygous for the recessive combination su shl wx c;

incorporating into said corn the fifth chromosome of Tripsacum to obtain an alien addition monosomic version thereof;

crossing said alien addition monosomic version with a sweet corn of genotype su Shl Wx C; and harvesting the progeny as seed.

13. The method of claim 12 including the further step of removing from the harvested progeny those seeds which exhibit, by aleurone color, the presence of said fifth chromosome of Tripsacum.

* * * * *